US005498401A

United States Patent [19]

Johnson et al.

[11] Patent Number: 5,498,401

[45] Date of Patent: Mar. 12, 1996

[54] DISPOSAL OF HYDRAZINE PROPELLANTS

[75] Inventors: Russell W. Johnson, Elmhurst, Ill.; Brent S. DeFeo, Sparta, N.J.; Francis S. Lupton, Evanston; Mark B. Koch, Mt. Prospect, both of Ill.

[73] Assignee: AlliedSignal Inc., Morris Township, Morris County, N.J.

[21] Appl. No.: 419,795

[22] Filed: Apr. 11, 1995

Related U.S. Application Data

[62] Division of Ser. No. 140,589, Oct. 21, 1993, Pat. No. 5,437,853.

[51] Int. Cl.[6] ............................ C01C 1/00; C07C 211/00

[52] U.S. Cl. ............................ 423/352; 564/463

[58] Field of Search ............................ 564/463; 423/352

[56] References Cited

U.S. PATENT DOCUMENTS 4,122,671 10/1978 Armstrong ................................ 60/218
4,661,179 4/1987 Hunter et al. ........................... 149/124

FOREIGN PATENT DOCUMENTS

0178001A1 4/1986 European Pat. Off. .
1595432 6/1970 France .
4131471A1 3/1993 Germany .

OTHER PUBLICATIONS

Rylinder, P. N., (Catalytic Hydrogenation over Platinum Metals Academic Press (1967).

Lunn G. et al. Reductive Destruction of Hydrazine as an Approach to Hazard Control Environ. Sc. Technol. 17, No. 4 (1983).

Database WPO Week 7425, Derwent Publications, London AN 74–45881V & JP, A. 48 099 092 (Tech. Res. & Dev.) Dec. 1973 Abstract.

*Primary Examiner*—Wayne Langel
*Attorney, Agent, or Firm*—Harold N. Wells; Roger H. Criss

[57] ABSTRACT

A method for converting hydrazine and/or substituted hydrazines, particularly unsymmetric dimethyl hydrazine (UDMH), to ammonia or ammonia and the corresponding amines by hydrogenation over a supported Group VIII metal catalyst. Preferably, the hydrazines are dissolved in a suitable solvent and then hydrogenated at a temperature of about 0° to 250° C., followed by separation of the commercially valuable ammonia and amines. Alternatively, a gas phase reaction may be used.

8 Claims, 2 Drawing Sheets

DISPOSAL OF HYDRAZINE PROPELLANTS

This application is a division of application Ser. No. 08/140,589, filed Oct. 21, 1993, U.S. Pat. No. 5,437,853.

BACKGROUND OF THE INVENTION

The invention relates generally to the disposal of energetic materials and more particularly to the deactivation of hydrazines, such as unsymmetric dimethyl hydrazine (UDMH) which are used as propellants. When combined with nitrogen tetroxide ($N_2O_4$) the reaction with UDMH releases a great amount of energy by the reaction:

$$N_2H_2(CH_3)_2+2N_2O_4 \rightarrow 3\ N_2+4H_2O+2\ CO_2$$

This reaction has been used in liquid fueled rockets and, consequently, the disposal of such hydrazines represents an important problem at the present time. Hydrazines alone may also be used as propellants where they are catalytically decomposed without oxidizers being present.

UDMH could be disposed of by incineration, decomposition in supercritical water, or by the above reactions, but it would be preferable if the products of the disposal method had commercial value. It was the purpose of the present inventors to develop a method for convenient disposal of hydrazine ($N_2H_4$) and substituted hydrazines such as UDMH which has the least adverse impact on the environment while at the same time produces valuable by-products.

It has been known that substituted hydrazines can be hydrogenated to ammonia and amines, see Catalytic Hydrogenation over Platinum Metals, Rylander, Academic Press 1967, p. 134–135.

Hydrogenolysis of substituted hydrazines over Rainey nickel catalysts was reported by Lunn et at. in Environ. Sci. Technol. Vol. 13, No. 4, 1983. Hydrogen was generated insitu by the reaction of KOH with an aluminum-nickel alloy.

Decomposition of hydrazine is discussed by Armstrong et al. in U.S. Pat. No. 4,122,671. Noble metal catalysts were shown to be effective so that no oxidizer was required.

Destruction of nitrogen-containing explosives has been the subject of various disclosures. German patent publication DE 413147-A1 discusses the hydrogenation of nitroaromatic explosives in the presence of a solvent, hydrogen, and a catalyst at a temperature of40°–100° C. U.S. Pat. No. 4,661,179 discloses a process for destroying waste explosives containing nitro, nitrate, or nitroamino groups.

SUMMARY OF THE INVENTION

Broadly, the invention is a method for disposal of hydrazine and substituted hydrazines to ammonia (from hydrazine) or ammonia and the corresponding amines (e.g. dimethyl amine from UDMH).

In one embodiment the process involves dissolving the hydrazine or substituted hydrazine in a suitable liquid carrier, such as water, alcohols, and hydrocarbons, e.g., methanol, toluene, or methylcyclohexane and then reacting the dissolved hydrazine or substituted hydrazine with hydrogen in a mixed phase reaction over a supported Group VIII metal catalyst at a temperature of about 0° to 250° C. The amine and ammonia are recovered and then the solvent and any unreacted hydrazine or substituted hydrazine may be returned to the process.

In an alternative embodiment the hydrazine or substituted hydrazine is evaporated into a carder gas such as nitrogen, steam, alcohols, or hydrocarbons and passed over the catalyst in the presence of hydrogen at temperatures such that the hydrazine is entirely in the vapor phase.

In one preferred embodiment, the invention is a method for convening unsymmetrical dimethyl hydrazine (UDMH) to dimethyl amine and ammonia, thereby producing valuable products and at the same time providing a means of disposing of UDMH.

Preferred Group VIII metals are platinum, palladium, nickel and cobalt, particularly palladium.

DESCRIPTION OF THE PREFERRED EMBODIMENTS

Hydrazines

Figure 1:
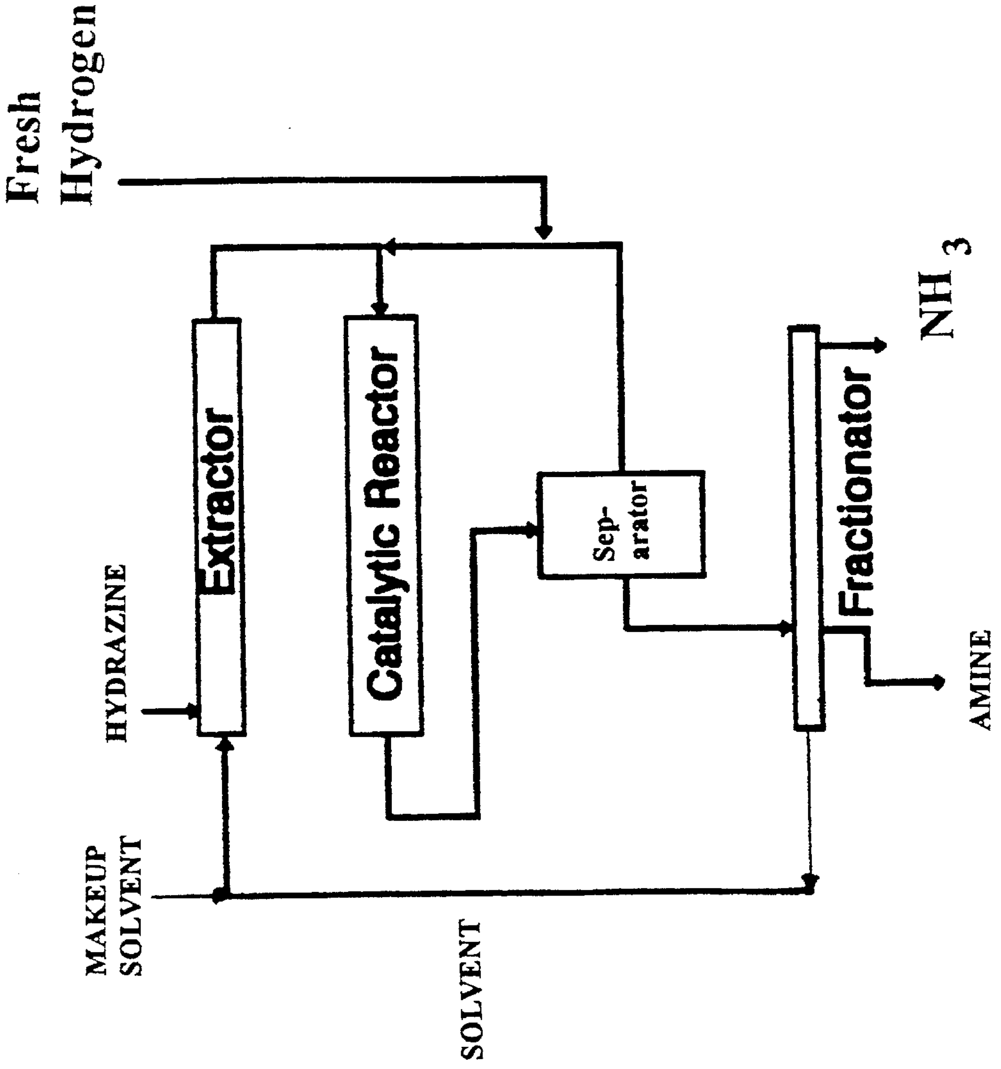
FIG. 1 is a flow sheet illustrating one process of the invention.

It should be understood that by the use of the term "hydrazine," not only the specific compound which is so-named and has the formula $N_2H_4$, but substituted hydrazines are subjects of the present invention. The later compounds may be generally described by the formula $R_1R_2NNR_3R_4$, where $R_1$, $R_2$, $R_3$, and $R_4$ are independently selected from hydrogen, alkyl, or aryl. Examples of such substituted hydrazines include alkyl hydrazines, for example, dimethyl hydrazine, diethyl hydrazine, and the like, aryl hydrazines for example, phenyl hydrazine or mixed substitutions such as methyl phenyl hydrazine. The most important substituted hydrazine is unsymmetrical dimethyl hydrazine $(CH_3)_2NNH_2$ since it is used as a propellant in large liquid-fueled rockets, either alone or in combination with hydrazine itself ($N_2H_4$). It will be appreciated that large amounts of such hydrazines have been produced. It has been an objective of the present inventors to provide a safe and convenient method of disposing of such materials. The present process has the additional advantage of producing commercially saleable products.

Catalysts

Group VIII metals are generally suitable for hydrogenation reactions particularly Pt, Pd, Ni, and Co. Although other hydrogenation catalysts may have use in the process of the invention, the noble metals of Group VIII are preferred, particularly Pd. The catalytic metals could be used alone in finely divided particulate form, but preferably they will be supported on solids such as carbon, alumina, silica or titania. In preferred embodiments the noble metal is deposited on a support in an amount between about 0.5 and 5 wt. % based on the finished catalyst. This may be accomplished by various techniques known to those skilled in the art, such as impregnation of the support with a solution of a noble metal compound followed by heating to decompose the noble metal compound, leaving a finely dispersed metal. Other methods may also be used such as coprecipitation of the metal compound and the support material from solution.

Mixed Phase Reaction

In a preferred embodiment, a solvent is used to dissolve and dilute the hydrazine or substituted hydrazine. The solvent chosen preferably will be selected from a group generally consisting of water, alcohols, and hydrocarbons. More particularly, the solvent should be capable of dissolving up to at least 50 wt. % of hydrazine, although typically the solvent will contain less than 30 wt. % hydrazine. Higher concentrations of hydrazine may be used if desired, up to substantially solvent-free hydrazines. Since the solvent among other things, serves to moderate the effect of the exothermic heat of reaction, it will be appreciated that selection of the amount of solvent will involve the design of the entire process. The solvent should be inert with respect to the hydrazine so that it acts as a carrier for the hydrazine and produces no undesirable by-products with it. Additionally, the solvent should not react significantly with hydrogen under conditions of the invention so that it can be recovered and recycled to the reaction without a need to remove hydrogenated by-products.

Considering the above requirements, the solvents which are preferred for the hydrogenation of hydrazine are hydrocarbons such as kerosine, naphtha, methylcyclohexane, decalin, and the like or alcohols such as methanol, ethanol and isopropanol, most preferably methylcyclohexane. Water is useful although less preferred since the products will contain water and may have to be dried.

While the solvents will ordinarily be selected because they are inert, it is possible to use a solvent which undergoes a reaction with hydrogen or which produces hydrogen. An example is methylcyclohexane, which can dehydrogenate when exposed to a noble metal catalyst, thus producing hydrogen for use in the reaction with the hydrazine, but also balancing the exothermic heat of reaction with the endothermic heat of the dehydrogenation.

Vapor Phase Reaction

In an alternative embodiment, the reaction is carried out in the vapor phase so that the solvents are no longer present, but instead a carrier gas such as nitrogen, steam, hydrocarbons, or alcohols are used to dilute the hydrazine or substituted hydrazine. The hydrazine and carrier gas mixture is combined with hydrogen and passed over the catalyst as in the preferred embodiment. Although the reaction is generally the same as in the case where solvents are used, the recovery of the products will differ.

Reaction Conditions

The reaction of a hydrogen with hydrazine produces ammonia and the corresponding amine where the hydrazine is substituted. For example, the reaction of UDMH with hydrogen may be written as follows:

$$N_2H_2(CH_3)_2 + H_2 \rightarrow NH(CH_3)_2 + NH_3$$

Hydrazine itself, $N_2H_4$, yields only ammonia. Hydrogenation of the hydrazine may be carded out at a temperature of about 0° to 250° C., preferably 100° to 150 ° C. A low temperature is preferred to avoid undue hydrogenation of the dimethyl amine and ammonia. However, practical considerations may require higher temperatures be used to obtain the optimum conversion of the hydrazine and selectivity to the desired products.

The reaction will generally be carded out with a positive pressure, preferably between about 50 to 500 psig (345–3450 kPa).

Hydrogen will be maintained at mol ratio of about 0.1 to 10/1 relative to the hydrazine. Although the reaction requires one mol of hydrogen for each mol of hydrazine reacted, lower amounts of hydrogen could be used to control the reaction, although the conversion necessarily is reduced. Under the reaction temperature and pressure the hydrazine containing solvent will be liquid and the hydrogen a gas so that a two-phase mixture will be passed over the supported catalyst at a liquid hourly space velocity based on the hydrazine of about 0.1 to 10 $hr^{-1}$, preferably between 1 and 5 $hr^{-1}$.

In the alternative embodiment where a vapor phase reaction is used, a single phase will be passed over the catalyst at a liquid hourly space velocity based on the hydrazine of about 0.1 to 10 $hr^{-1}$, preferably between 1 and 5$hr^{-1}$.

Process Description

FIG. 1 illustrates generally the process of the invention where a liquid carder is used. The hydrazine to be converted to less energetic materials, that is, ammonia and the corresponding amine, is first removed from its container, (not shown) and dissolved in the selected solvent. The hydrazines of interest generally will be liquids at ambient conditions and can be pumped into an extraction column as shown or similar mixing vessel. The dilution of the hydrazine will assist in controlling the exothermic heat of the hydrogenolysis reaction. Accordingly, the hydrazine and the solvent will be metered to provide the desired concentration, generally up to about 30 weight percent at the outlet of the extractor. Since the catalytic reaction will ordinarily not be complete, the recycled solvent will contain a significant amount of the unreacted hydrazine. Thus, the fresh hydrazine would be added at the rate needed to makeup for the hydrazine converted and to provide a constant concentration at the inlet of the catalytic reactor.

The solvent containing diluted hydrazine is passed to a catalytic reactor along with added hydrogen over the supported Group VIII metal catalyst to convert the hydrazine to ammonia and the corresponding amine (where the hydrazine was substituted). The amount of hydrogen is metered to provide the desired tool ratio of hydrogen to hydrazine, that is 0.1/1 to 10/1. If desired, the amount of hydrogen may be limited to only that required to react with the hydrazine. However, in most cases an excess will be used and the unreacted hydrogen will be separated at the outlet of the reactor and recycled as shown.

The reactor may be of various types known in the art where solid catalysts are contacted with liquid, gas, or mixed phase streams. Since the heat of reaction is substantial, it must be removed to control the reaction and to assure that the desired products are obtained. Thus, heat removal means are preferred which could include internal cooling coils, but preferably the reactor is constructed in the form of a shell and tube heat exchanger. The catalyst would be disposed within the tubes and the shell side would be filled with the cooling fluid. Since the reaction temperature is relatively low (about 100° to 150° C.) cooling by water may be sufficient. Alternatively, silicone fluids, hydrocarbons, and the like could be used.

After leaving the reactor, the mixed-phase stream passes to a separator where excess hydrogen is removed and the liquid phase then is passed to a fractionator for removing the ammonia and any amines produced. Typically, a distillation column will be used. The solvent is removed from the bottom of the column to dissolve fresh hydrazine.

Figure 2:
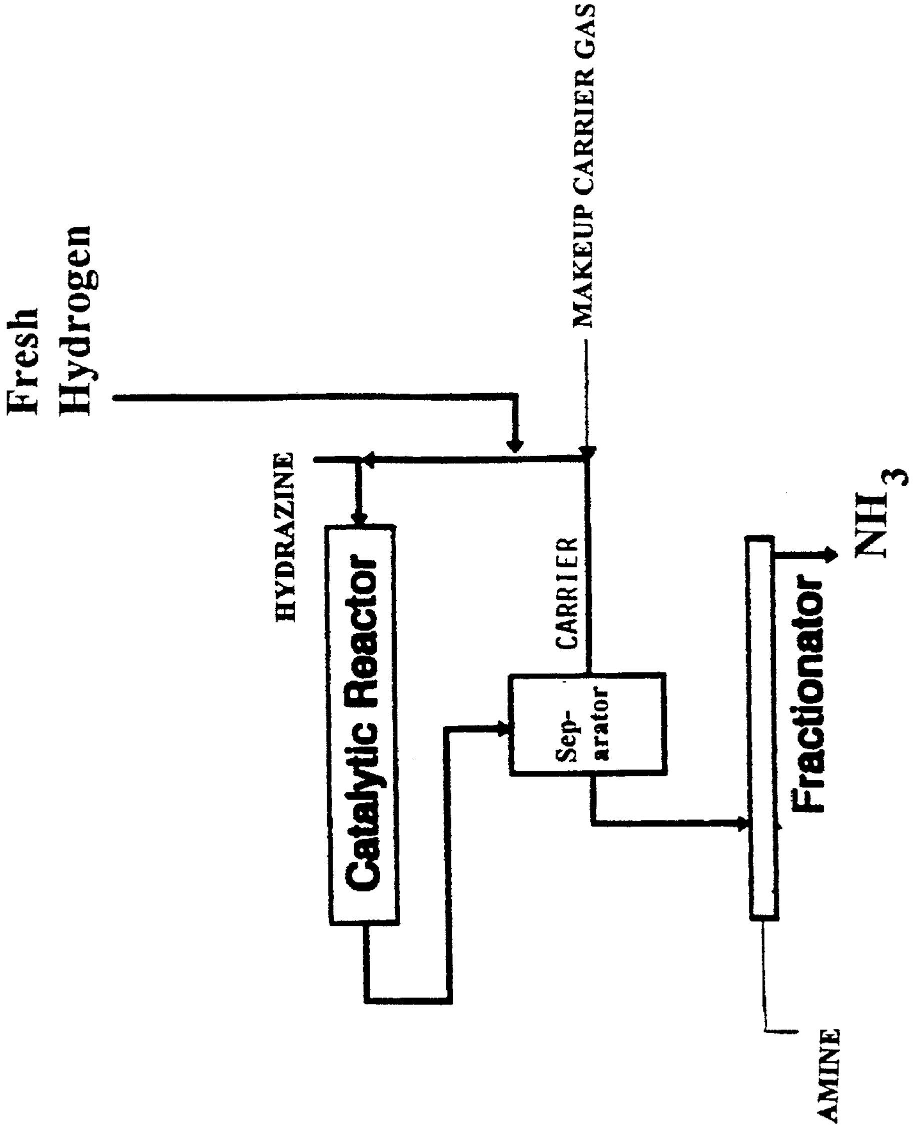
FIG. 2 is a flow sheet illustrating an alternative process of the invention.

FIG. 2 illustrates an alternative embodiment where a gas phase reaction is used. Fresh hydrazine and hydrogen are added to a circulating gas stream which is principally the carrier gas plus hydrogen, and unreacted hydrazine. After passing over the catalyst, the effluent stream is condensed and separated, with the gas phase being recycled and the liquid phase being fractionated to separate the ammonia from the amine product. In the case where the compound $N_2H_4$ is being hydrogenated the effluent stream might be scrubbed, for example with water to separate the ammonia from the recycled gases.

EXAMPLE 1

Hydrogenation of unsymmetrical dimethylhydrazine (UDMH) was carried out in a batch reaction. three grams (3 g) of UDMH dissolved in 150 g water (2 wt. %) was placed in a 400 mL Parr autoclave. One g of 1 wt. % Pd on a steam-activated carbon granules (AESAR, Johnson Matthey, Inc.) was added. After flushing the reactor with nitrogen, the nitrogen was replaced with hydrogen and pressured to 275 psig (1897 kPa). Then the reactor was heated to the desired temperature with stirring and held at constant conditions for 3 hours until the reaction was substantially complete. The pressure rose to about 340 psig (2344 kPa). The reactor then was cooled to less than 10° C. in an ice bath and then emptied for analysis. The reactor was vented to atmospheric pressure with the gases passing through an acid scrubber containing 2 wt. % HCl. The dimethylamines were measured by ion chromatography of the liquids in the reactor and the acid scrubber. The yield of dimethyl amine was calculated from the amount of dimethylamine (DMA) found by analysis.

EXAMPLE 2

The procedure of Example 1 was repeated using toluene as the solvent. Test 8 was carried out for 6 hours and Test 9 for 2 hours rather than 3 hours as in the previous seven tests and the concentration of UDMH was increased to 5 wt. %. Here, dimethylamine was analyzed by gas chromatography and mass spectroscopy.

The results obtained in Examples 1 and 2 are summarized in the following table.

TABLE A

| Test No. | Temp, °C. | Solvent | UDMH (wt. %) | Catalyst Type | Yield of DMA % |
|---|---|---|---|---|---|
| 1 | 85 | water | 2 | None | 1.5 |
| 2 | 60 | " | 2 | 2% Pd on C | 6.4 |
| 3 | 85 | " | 2 | " | 16.4 |
| 4 | 105 | " | 2 | " | 30 |
| 5 | 105 | " | 2 | " | 23.6 |
| 6 | 105 | toluene | 2 | 2% Pd on C | 38. |
| 7 | 105 | " | 2 | " | 40. |
| 8 | 150 | " | 5 | " | 59 |
| 9 | 150 | " | 5 | " | 81 |

It may be concluded from the above results that the conversion of UDMH and the yield of DMA increases with temperature as might be expected. The actual temperature used for large scale applications of the process would be selected depending on various factors, such as the extent of byproduct formation, costs of utilities for heating and cooling, and ease of separation of the products from the solvent. The catalyst, solvent, and hydrazine concentration would be selected based on similar considerations.

We claim:

1. A method of converting hydrazines to ammonia or ammonia and the corresponding amines comprising:

(a) evaporating the hydrazine into a suitable carder gas;

(b) passing said evaporated hydrazine of (a) over a supported metal from Group VIII at a temperature of 0° to 250° C. in the presence of at least 0.1 mols of hydrogen for each mol of hydrazine, so as to produce by hydrogenolysis ammonia or ammonia and or ammonia the corresponding amine;

(c) recovering the ammonia and amine from the product of (b).

2. The method of claim 1 wherein said carrier gas is at least one member of the group consisting of nitrogen, steam, hydrocarbons, and alcohols.

3. The method of claim 1 wherein the product of (b) is condensed to recover said ammonia and amine.

4. The method of claim 1 wherein said hydrazine is hydrazine, dimethyl hydrazine, or a mixture thereof.

5. The method of claim 1 wherein said Group VIII metal is at least one member of the group consisting of Pt, Pd, Ni, and Co.

6. The method of claim 5 wherein said Group VIII metal is Pd.

7. The method of claim 1 wherein said Group VIII metal is supported on a member of the group consisting of carbon, alumina, silica, and titania.

8. The method of claim 7 wherein said Group VIII metal is supported on carbon.

* * * * *

UNITED STATES PATENT AND TRADEMARK OFFICE

CERTIFICATE OF CORRECTION

PATENT NO. : 5,498,401

DATED : March 12, 1996

INVENTOR(S) : Russell W. Johnson et al.

It is certified that error appears in the above-identified patent and that said Letters Patent is hereby corrected as shown below:

Column 1, line 66: "carder" should read --carrier--
Column 2, line 4: "convening" should read --converting--
Column 3, line 45: "carrier" should read --carried--.
line 52: "carrier" should read --carried--.
Column 4, line 5: "carder" should read --carrier--
line 27: "tool" should read --mol--
Column 6, line 14: "carder" should read --carrier--
line 22: after "ammonia" insert --or ammonia--
line 22: before "amine" insert --the corresponding--

Signed and Sealed this

Thirtieth Day of July, 1996

Attest:

BRUCE LEHMAN

Attesting Officer

Commissioner of Patents and Trademarks